US012383765B2

(12) United States Patent
Lansonneur et al.

(10) Patent No.: US 12,383,765 B2
(45) Date of Patent: Aug. 12, 2025

(54) BIOLOGICAL EQUIVALENT DOSE INFORMED FLASH RADIATION THERAPY

(71) Applicant: Siemens Healthineers International AG, Steinhausen (CH)

(72) Inventors: Pierre Lansonneur, Lyons (FR); Michael Folkerts, Costa Mesa, CA (US); Miriam Krieger, Halle (DE)

(73) Assignee: Siemens Healthineers International AG, Steinhausen (CH)

( * ) Notice: Subject to any disclaimer, the term of this patent is extended or adjusted under 35 U.S.C. 154(b) by 277 days.

(21) Appl. No.: 18/207,404

(22) Filed: Jun. 8, 2023

(65) Prior Publication Data

US 2024/0408412 A1 Dec. 12, 2024

(51) Int. Cl.
*A61N 5/10* (2006.01)

(52) U.S. Cl.
CPC ......... *A61N 5/1031* (2013.01); *A61N 5/1045* (2013.01); *A61N 5/1047* (2013.01); *A61N 5/1071* (2013.01); *A61N 5/1081* (2013.01); *A61N 2005/1074* (2013.01); *A61N 2005/1087* (2013.01); *A61N 2005/1089* (2013.01)

(58) Field of Classification Search
CPC ........ A61N 5/10; A61N 5/103; A61N 5/1031; A61N 5/1037; A61N 5/1038; A61N 2005/1041; A61N 5/1042; A61N 5/1043; A61N 5/1044; A61N 5/1045; A61N 5/1047; A61N 5/1048; A61N 5/1049; A61N 2005/1052; A61N 2005/1055; A61N 2005/1059; A61N 2005/1061; A61N 2005/1062; A61N 5/1064; A61N 5/1065; A61N 5/1067; A61N 5/1068; A61N 5/1071; A61N 2005/1072; A61N 2005/1074; A61N 5/1077; A61N 5/1081; A61N 5/1082; A61N 2005/1087; A61N 2005/1089
USPC .......................................................... 378/65
See application file for complete search history.

(56) References Cited

U.S. PATENT DOCUMENTS

| | | | | |
|---|---|---|---|---|
| 7,206,377 B2 * | 4/2007 | Svatos | ................... | A61N 5/103 378/65 |
| 7,519,150 B2 * | 4/2009 | Romesberg, III | .... | A61N 5/1031 378/65 |
| 7,551,717 B2 * | 6/2009 | Tomé | ................... | A61B 5/6831 378/65 |
| 7,831,289 B2 * | 11/2010 | Riker | ..................... | G16H 70/20 378/65 |

(Continued)

OTHER PUBLICATIONS

Krieger, Miriam et al.; A quantitative FLASH effectiveness model to reveal potentials and pitfalls of high dose rate proton therapy. Medical Physics, 49(3), 2026-2038, Dec. 2021.

(Continued)

*Primary Examiner* — Allen C. Ho
(74) *Attorney, Agent, or Firm* — Fitch, Even, Tabin & Flannery LLP (57) ABSTRACT

A control circuit accesses information representing radiation dose deposition as a function of time for a particular patient as well as at least one biological parameter for that particular patient. The control circuit then determines a biological equivalent dose for the particular patient as a function of both the information representing radiation dose deposition as a function of time and the at least one biological parameter to provide a determined biological equivalent dose for the particular patient.

23 Claims, 4 Drawing Sheets

(56) References Cited

U.S. PATENT DOCUMENTS

| | | | | |
|---|---|---|---|---|
| 7,835,493 | B2* | 11/2010 | Keall | A61N 5/1042 378/65 |
| 9,192,782 | B1* | 11/2015 | Grimm | A61N 5/1031 |
| 9,289,627 | B2* | 3/2016 | Otto | A61N 5/1031 |
| 9,387,344 | B2* | 7/2016 | Sgouros | A61B 6/5217 |
| 9,387,345 | B2* | 7/2016 | Nord | A61N 5/1031 |
| 9,486,649 | B2* | 11/2016 | Bert | A61N 5/107 |
| 9,597,529 | B2* | 3/2017 | Lidestri | A61N 5/1043 |
| 9,839,793 | B2* | 12/2017 | Harada | A61N 5/1075 |
| 10,029,121 | B2* | 7/2018 | Li | A61B 5/055 |
| 10,076,673 | B2* | 9/2018 | Ranganathan | A61N 5/1077 |
| 10,166,404 | B2* | 1/2019 | Gemmel | A61N 5/1048 |
| 10,252,081 | B2* | 4/2019 | Kauppinen | A61N 5/1042 |
| 10,441,819 | B2* | 10/2019 | Sayeed | A61N 5/1071 |
| 10,456,600 | B2* | 10/2019 | Owens | A61N 5/1081 |
| 10,556,124 | B2* | 2/2020 | Zhang | A61N 5/1047 |
| 10,556,125 | B2* | 2/2020 | Kuusela | A61N 5/1031 |
| 10,688,320 | B2* | 6/2020 | Voronenko | A61N 5/1045 |
| 10,702,708 | B2* | 7/2020 | Miettinen | A61N 5/1031 |
| 10,828,511 | B2* | 11/2020 | Zhang | A61N 5/1031 |
| 10,918,886 | B2* | 2/2021 | Smith | G16H 50/50 |
| 10,940,334 | B2* | 3/2021 | Fishman | A61N 5/1083 |
| 11,065,471 | B2* | 7/2021 | Wu | G16H 20/40 |
| 11,090,508 | B2* | 8/2021 | Folkerts | A61N 5/1031 |
| 11,103,727 | B2* | 8/2021 | Folkerts | G06T 7/0012 |
| 11,167,153 | B2* | 11/2021 | Bokrantz | A61N 5/1031 |
| 11,291,861 | B2* | 4/2022 | Cooley | A61N 5/1045 |
| 11,517,766 | B2* | 12/2022 | Bzdusek | A61N 5/1039 |
| 11,541,252 | B2* | 1/2023 | Folkerts | G16H 20/40 |
| 11,559,701 | B2* | 1/2023 | Fan | A61N 5/1075 |
| 11,590,363 | B2* | 2/2023 | Petaja | G16H 30/40 |
| 11,612,765 | B2* | 3/2023 | Fallone | A61N 5/107 600/427 |
| 11,642,550 | B2* | 5/2023 | Peltola | A61N 5/103 378/65 |
| 11,648,418 | B2* | 5/2023 | Owens | A61N 5/1039 378/65 |
| 11,654,299 | B2* | 5/2023 | Nord | A61N 5/103 378/65 |
| 11,679,273 | B2* | 6/2023 | Kauppinen | A61N 5/1031 600/1 |
| 11,786,753 | B2* | 10/2023 | Traneus | A61N 5/103 600/1 |
| 11,786,755 | B2* | 10/2023 | Ohishi | A61N 5/1039 600/1 |
| 11,813,479 | B2* | 11/2023 | Czeizler | A61N 5/103 |
| 11,826,560 | B2* | 11/2023 | Zhang | A61N 5/1031 |
| 11,839,776 | B2* | 12/2023 | Eriksson | A61N 5/1037 |
| 11,938,341 | B2* | 3/2024 | Hirvonen | A61N 5/1031 |
| 11,992,703 | B2* | 5/2024 | Lansonneur | A61N 5/1071 |
| 12,059,577 | B2* | 8/2024 | Peltola | A61N 5/1036 |
| 12,115,386 | B2* | 10/2024 | Voronenko | A61N 5/1043 |
| 12,138,472 | B2* | 11/2024 | Labarbe | A61N 5/10 |
| 12,138,476 | B2* | 11/2024 | Czeizler | A61N 5/1031 |
| 12,138,477 | B2* | 11/2024 | Ropo | A61N 5/1048 |
| 12,138,478 | B2* | 11/2024 | Peltola | A61N 5/1031 |
| 12,138,480 | B2* | 11/2024 | Zhang | A61N 5/1031 |
| 12,138,483 | B2* | 11/2024 | Czeizler | A61N 5/1031 |
| 12,145,001 | B2* | 11/2024 | van den Heuvel | G16H 20/40 |
| 12,157,013 | B2* | 12/2024 | Peltola | A61N 5/103 |
| 12,168,145 | B2* | 12/2024 | Korhonen | A61N 5/1039 |
| 12,179,038 | B2* | 12/2024 | Fredriksson | A61N 5/103 |
| 2009/0052623 | A1 | 2/2009 | Tome | |
| 2016/0287903 | A1 | 10/2016 | Sgouros | |
| 2021/0128946 | A1 | 5/2021 | Smith | |
| 2021/0346719 | A1 | 11/2021 | Folkerts | |
| 2021/0393982 | A1 | 12/2021 | Lansonneur | |
| 2021/0402213 | A1 | 12/2021 | Labarbe | |
| 2022/0296927 | A1 | 9/2022 | Cooley | |
| 2022/0409927 | A1 | 12/2022 | Petaja | |
| 2023/0115222 | A1 | 4/2023 | Traneus | |

OTHER PUBLICATIONS

Mazal, Alejandro et al.; FLASH and minibeams in radiation therapy: the effect of microstructures on time and space and their potential application to protontherapy. British Institute of Radiology, 2020;93:110720190807, 17 pages.

Petersson, Kristoffer et al., A Quantitative Analysis of the Role of Oxygen Tension in FLASH Radiation Therapy. International Journal of Radiation Oncology Biology Physics. 2020; 107(3):539-547.

Extended European Search Report from related European Patent Application No. 24180112.5 dated Aug. 26, 2024; 11 pages.

* cited by examiner

BIOLOGICAL EQUIVALENT DOSE INFORMED FLASH RADIATION THERAPY

TECHNICAL FIELD

These teachings relate generally to treating a patient's planning target volume with energy pursuant to an energy-based treatment plan and more particularly to FLASH radiation therapy treatment plans.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

Many radiation treatment plans specify values for each of a variety of treatment-platform parameters during a single field or during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

FLASH energy treatment is a known area of prior art endeavor, albeit a relatively new area of consideration. FLASH radiotherapy is a technique (at least for photon, electron, and proton treatments) that employs very brief, very high dose rates (utilizing large beam currents). FLASH treatments hold the promise of shortening treatment time to just one to three 1-second sessions while also potentially reducing side effects, perhaps considerably. For example, a significant sparing of normal tissue notwithstanding iso-effective tumor growth delay has been demonstrated through very brief irradiation at dose rates on the order of 40 Gy/s. This sparing of normal tissue has been dubbed the FLASH effect.

Unfortunately, the applicant has determined that there is much unknown about FLASH treatments, including how to take into account one or more biological effects pertaining to a patient when prescribing a FLASH treatment, optimizing a FLASH treatment, quality checking a FLASH treatment plan, and/or administering a FLASH treatment plan.

BRIEF DESCRIPTION OF THE DRAWINGS

The above needs are at least partially met through provision of the biological equivalent dose informed FLASH radiation therapy described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments, a control circuit accesses information representing radiation dose deposition as a function of time for a particular patient as well as at least one biological parameter for that particular patient. The control circuit then determines a biological equivalent dose for the particular patient as a function of both the information representing radiation dose deposition as a function of time and the at least one biological parameter to provide a determined biological equivalent dose for the particular patient.

By one approach, the foregoing accommodates determining a plurality of biological equivalent doses for the particular patient.

By one approach, the aforementioned information representing radiation dose deposition as a function of time comprises both dose and dose rate information.

By one approach, the aforementioned at least one biological parameter comprises at least one of:
  normal tissue complication probability information;
  oxygen level information;
  linear energy transfer information;
  an identified tissue;
  an identified organ;
  a specified portion of an identified organ;
  a temporal-based parameter;
  radiosensitivity of a given tissue/organ;
  patient image information;
  a tissue type;
  a blood oxygen level;
  a blood type;
  a medication;
  chemotherapy information;
  prior surgery information;
  immunotherapy information;
  prior medical treatment information;

demographic information;
biological age information;
genetic marker information;
a time of day;
a tumor type;
pH (potential hydrogen) balance information;
temperature information;
blood pressure information;
blood panel information; and/or
immunity health information.

By one approach, these teachings will further accommodate any one or more of:

generating a radiation treatment prescription as a function, at least in part, of the determined biological equivalent dose for the particular patient;

optimizing a FLASH radiation therapy treatment as a function, at least in part, of the determined biological equivalent dose for the particular patient to provide an optimized FLASH radiation therapy treatment;

quality evaluating an optimized FLASH radiation therapy treatment plan as a function, at least in part, of the determined biological equivalent dose for the particular patient; and/or administering radiation to the particular patient as a function of the aforementioned optimized FLASH radiation therapy treatment plan.

So configured, these teachings can capture the joint effect of dose distributions, dose-rate distributions, and one or more items of relevant biological data into one metric that correlates to the effects observed at a biological level.

Figure 1:
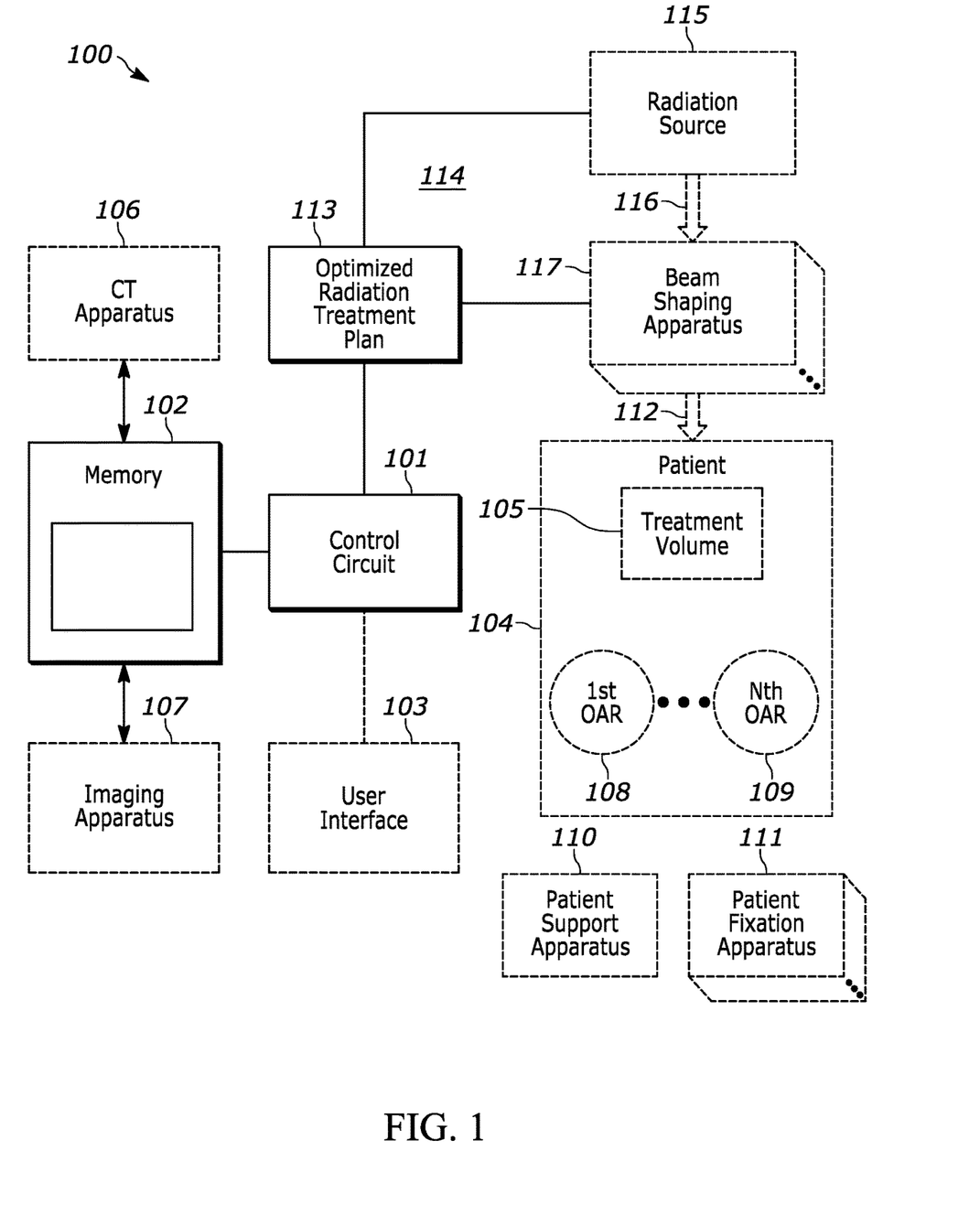
FIG. 1 comprises a block diagram as configured in accordance with various embodiments of these teachings.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient, information regarding a particular radiation treatment platform, information representing radiation dose deposition as a function of time for the particular patient, and at least one biological parameter for the particular patient as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. (It should be noted that these teachings are also applicable to a plan that makes use of only a single "field," as when, for example, the gantry is constantly in motion and radiation is constantly applied.) In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116. By one approach this energy-based treatment platform 114 is particularly configured to deliver FLASH radiation therapy.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
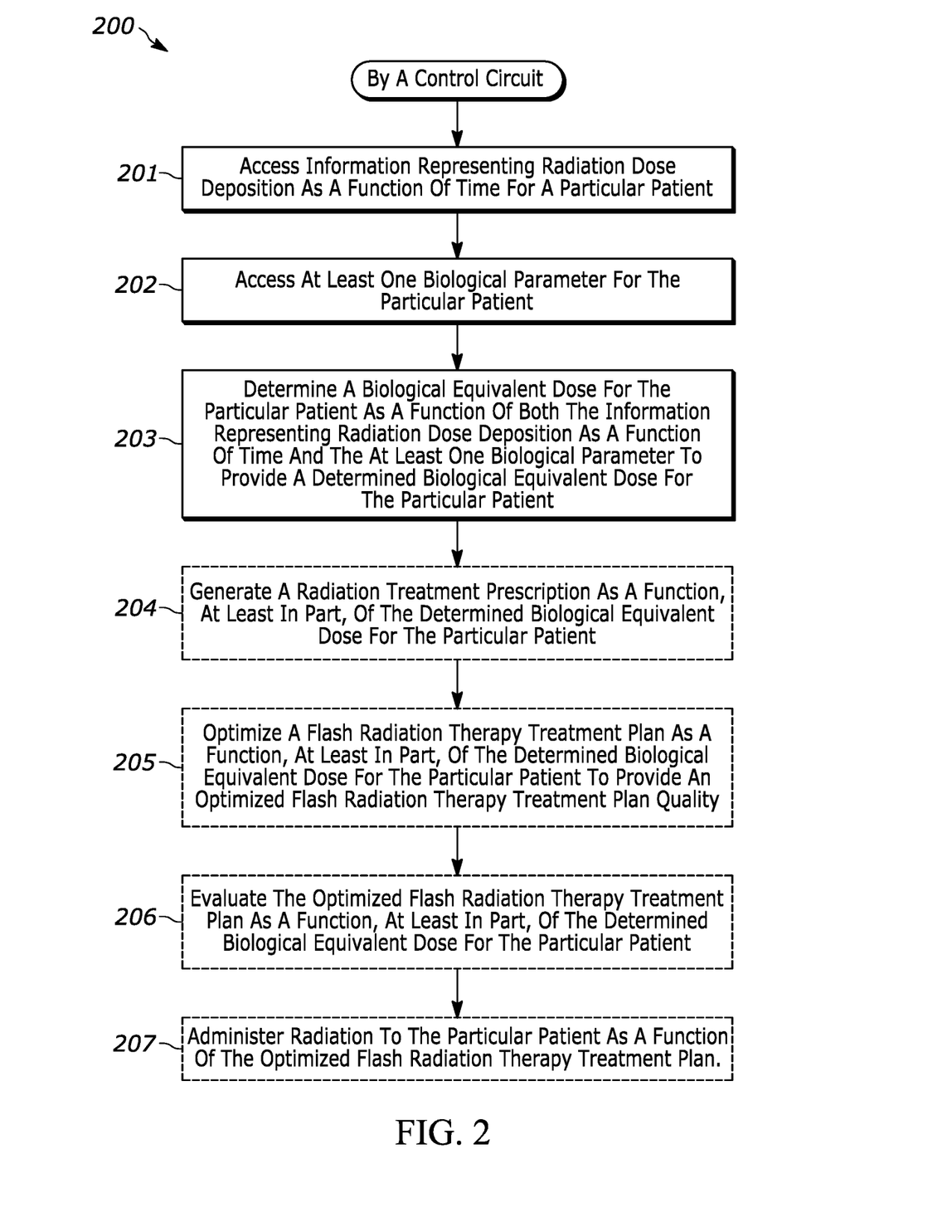
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 can serve to facilitate generating an optimized radiation treatment plan 113 to thereby facilitate treating a particular patient with therapeutic radiation (and in particular FLASH radiation therapy) using a particular radiation treatment platform per that optimized radiation treatment plan.

At block 201, this process 200 provides for accessing information representing radiation dose deposition as a function of time for a particular patient. By one approach, this information comprises both dose and dose rate information.

At block 202, the control circuit 101 accesses at least one biological parameter for the particular patient. These teachings are highly flexible in practice and will accommodate a wide variety of biological parameters. Examples of possibly beneficial biological parameters include, but are not limited to, any one or more of:

normal tissue complication probability information (corresponding, for example, to an effect that is measured but which is not necessarily an input of the biological equivalent dose);

oxygen level information (including, for example, a general oxygen level in a given tissue or anatomical structure, an oxygen level in the patient's blood, and/or even down to oxygen levels at a per-voxel or a sub-group-of-voxels level);
linear energy transfer information;
an identified tissue;
an identified organ;
a specified portion of an identified organ;
a temporal-based parameter;
radiosensitivity of a given tissue/organ (which information captures, for example, the alpha/beta ratio of a given organ);
patient image information (including but not limited to imaging derived from computed tomography, magnetic resonance imaging, and/or positron emission tomography, as well as imaging that presents segmentation information regarding the patient);
a tissue type;
a blood oxygen level;
a blood type;
a medication (including one or more prescription or non-prescription medicines and/or supplements);
chemotherapy information (including previous chemotherapy treatments, current chemotherapy treatments, and/or planned/scheduled chemotherapy treatments);
prior surgery information;
immunotherapy information;
prior medical treatment information (including, for example, radio therapy, ultrasound, and so forth);
demographic information (such as, but not limited to, age, sex, ethnicity, health factors (such as body mass index, autoimmune conditions, blood sugar levels, hemophilia, high blood pressure, and so forth), lifestyle factors (such as smoking and alcohol history and practices), stress factors, blood panel information (such as white blood cell count, cholesterol levels, and so forth), and even DNA information);
biological age information;
genetic marker information;
a time of day;
a tumor type;
pH (potential hydrogen) balance information;
temperature information;
blood pressure information;
blood panel information; and/or
immunity health information.

At block 203, the control circuit 101 then determines a biological equivalent dose for the particular patient as a function of both the information representing radiation dose deposition as a function of time and the at least one biological parameter to thereby provide a determined biological equivalent dose for the particular patient. By one approach, this can comprise determining a plurality of biological equivalent doses for the particular patient to thereby provide a plurality of determined biological equivalent doses for the particular patient.

By one approach, the foregoing comprises determining at least one biological equivalent dose on a per voxel basis (for example, for voxels within a patient target volume and/or within an organ-at-risk). The latter can be useful, for example, when the dose versus time information comprises a set of three-dimensional points within a patient image. By another approach, the foregoing may comprise determining at least one biological equivalent dose on a per patient structure basis.

Figure 3:
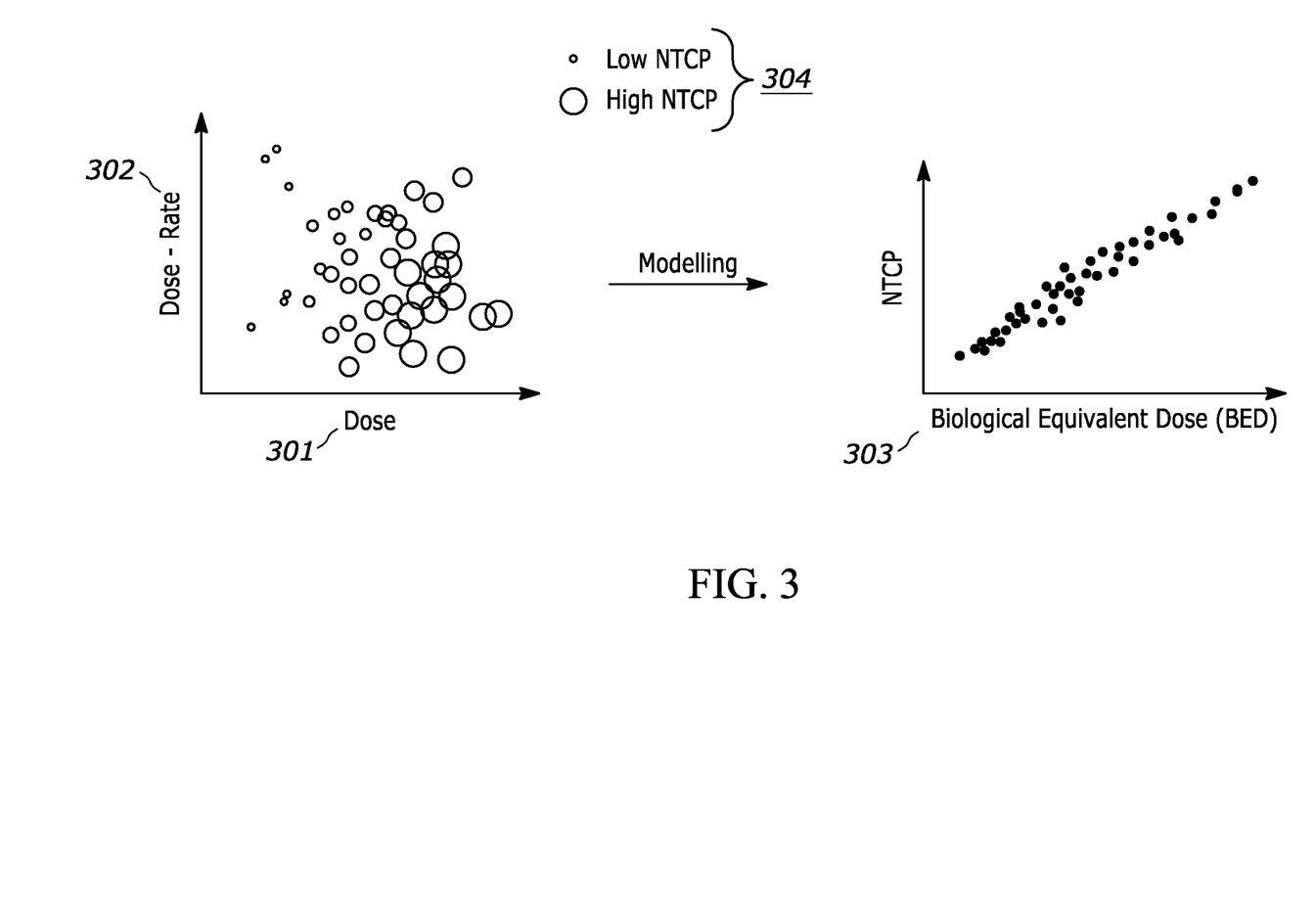
FIG. 3 comprises graphs as configured in accordance with various embodiments of these teachings.

FIG. 3 presents an illustrative example in these regards, it being understood that the details of this example are intended to serve an illustrative purpose and are not intended to suggest any limitations with respect to these teachings.

In this example, the dose 301 and dose-rate 302 distributions are combined into a biological equivalent dose (BED) 303 that correlates with Normal Tissue Complication Probability (NTCP) 304. The relationship between dose (D) 301, dose-rate (DR) 302 and Normal Tissue Complication Probability (NTCP) 304 is complex and not necessarily intuitive. It will be appreciated that combining the dose and dose rate into one distribution BED=f(D,DR) allows better visualizations of their correlations with NTCP.

As noted above, these teachings will accommodate using any of a variety of biological inputs. As but one illustrative example, the level of oxygen within a tissue can be used in conjunction with the dose-rate information to generate an oxygen enhancement ratio weighted biological dose.

By one optional approach, referring to optional block 204, these teachings will accommodate generating a radiation treatment prescription as a function, at least in part, of the above-described biological equivalent dose for the particular patient. Those skilled in the art will understand that the radiation treatment prescription expresses the general dosing goals envisioned and intended by a prescribing oncologist. A radiation treatment prescription is accordingly silent regarding such things as treatment machine geometry, control points, treatment fields, and so forth. (To be clear, it will be understood that radiation treatment prescriptions are different from optimization objectives, the latter being very much specifically designed to reflect and accommodate the technical details and specifications of a particular radiation treatment platform, specific details regarding the patient's presentation, and/or other physical details pertaining to a particular application setting treatment machine geometry, control points, treatment fields, and so forth.)

In lieu of the foregoing, or in combination therewith, by another optional approach and as expressed at optional block 205, these teachings will accommodate optimizing a FLASH radiation therapy treatment plan as a function, at least in part, of the determined biological equivalent dose for the particular patient to provide an optimized FLASH radiation therapy treatment plan. By one approach, the foregoing can comprise calculating a plurality of biological equivalent dose values as part of the optimization loop. These different biological equivalent dose values may correspond to different patient structures, patient sub-structures, and/or voxels and may be included as part of a cost function that is iteratively reduced to a local (if not global) minimum. For example, a biological equivalent dose value AB can be iteratively generated until a seemingly most optimal value is found.

When optimizing a FLASH plan, better performances may be expected when the analytical expression of the gradient, i.e., the derivative of the distribution to optimize with respect to the optimization variables, is known. Generally speaking, the variables to optimize include the beamlet intensities for Intensity Modulated Radiotherapy or the weights of the individual pencil beams for Intensity Modulated Proton Therapy. In both cases, the optimization variables can be expressed in Monitor Units (MU). For a model where the BED depends on the dose-rate DR and the dose D only, the gradient with respect to the optimization variables MU can be expressed as:

$$\frac{\partial BED}{\partial MU} = \frac{\partial BED}{\partial D} \cdot \frac{\partial D}{\partial MU} + \frac{\partial BED}{\partial DR} \cdot \frac{\partial DR}{\partial MU}.$$

For a model where the BED depends on the dose-rate DR, the dose D and any other biological metric X (e.g., the oxygen enhancement ratio, or the linear energy transfer), the gradient with respect to the optimization variables MU can be expressed as:

$$\frac{\partial BED}{\partial MU} = \frac{\partial BED}{\partial D} \cdot \frac{\partial D}{\partial MU} + \frac{\partial BED}{\partial DR} \cdot \frac{\partial DR}{\partial MU} + \frac{\partial BED}{\partial X} \cdot \frac{\partial X}{\partial MU}.$$

These teachings will also accommodate allowing the BED to be a function of dose vs. delivery time curve, in which case, the impact on BED for a given dose delivery sequence could be evaluated with the aid of detailed treatment delivery modeling. Likewise, the chain rule still applies, and includes the proton pencil beam spot list (scan pattern) as a variable that can be manipulated by the optimizer to achieve a BED goal.

In lieu of the foregoing, or in any permutation or combination therewith, at optional block 206 this process 200 will accommodate quality evaluating an optimized FLASH radiation therapy treatment plan as a function, at least in part, of the determined biological equivalent dose for the particular patient. Such an approach may be beneficial when, for example, the biological equivalent dose corresponds to a three-dimensional distribution and quality is evaluated, at least in part, using that distribution as an input.

And again in lieu of the foregoing, or in any permutation or combination therewith, at optional block 207 these teachings will accommodate administering radiation to the particular patient as a function of the aforementioned optimized FLASH radiation therapy treatment plan using, for example, the above-described radiation treatment platform 114.

To assist the treatment planner, these teachings will also accommodate providing one or more corresponding evaluation tools. Examples include, but are not limited to, biological equivalent dose volume histograms, biological equivalent dose distribution displayed on top of computed tomography images, biological equivalent dose distribution displayed per field, biological equivalent dose influence matrices, and so forth.

Figure 4:
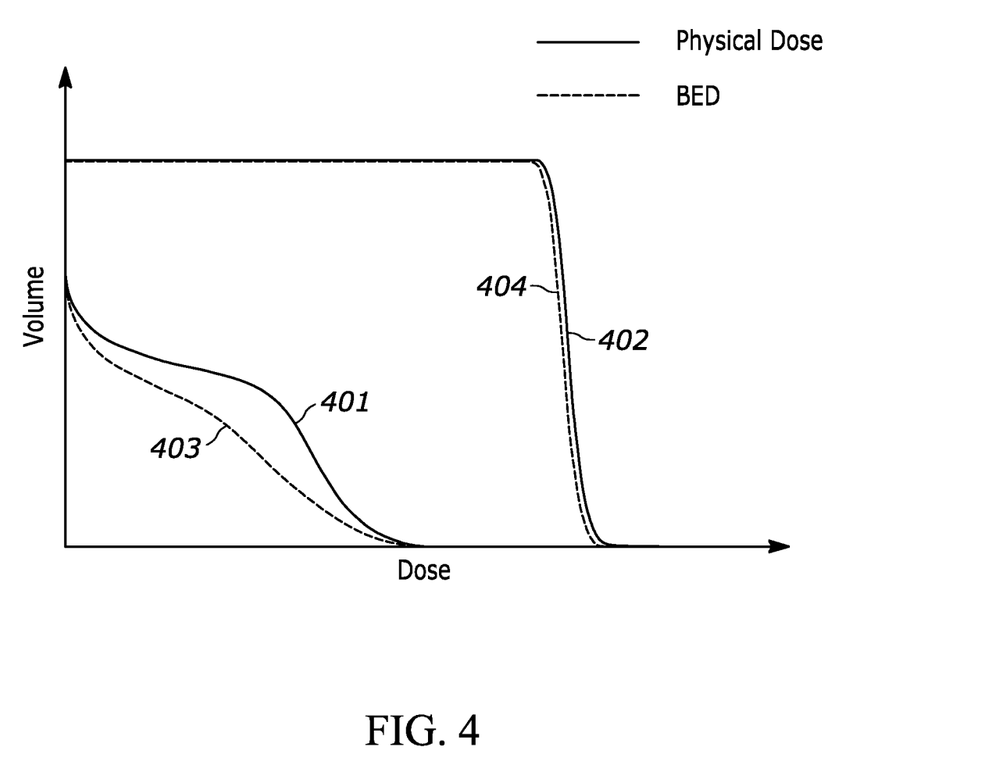
FIG. 4 comprises a graph as configured in accordance with various embodiments of these teachings.

By way of illustration, and referring to FIG. 4, a standard dose volume histogram (DVH) 401, 402 can be presented along with a biological equivalent dose volume histogram (BEDVH) 403, 404 for an organ at risk and a target volume, respectively. The target coverage is relatively unchanged, but the BED received by the organ-at-risk is significantly lower as compared with the physical dose. This interface facilitates clinical decision making with respect to the treatment modality (FLASH as versus conventional).

It will be appreciated that, while existing FLASH radiation therapy treatment plan optimization techniques tend to focus only on improving physical dose rates, such existing approaches also tend to neglect consideration of any FLASH-based biological effects; the present teachings, however, successfully attend to both considerations.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method comprising:
by a control circuit:
accessing information representing a radiation dose deposition as a function of time for a particular patient;
accessing at least one biological parameter for the particular patient; and
determining a biological equivalent dose for the particular patient as a function of both the information representing a radiation dose deposition as a function of time for the particular patient and the at least one biological parameter for the particular patient to provide a determined biological equivalent dose for the particular patient.

2. The method of claim 1, wherein determining a biological equivalent dose for the particular patient comprises determining a plurality of biological equivalent doses for the particular patient as a function of both the information representing a radiation dose deposition as a function of time for the particular patient and the at least one biological parameter for the particular patient to provide a plurality of determined biological equivalent doses for the particular patient.

3. The method of claim 1, wherein the information representing a radiation dose deposition as a function of time for the particular patient comprises both dose information and dose rate information.

4. The method of claim 1, wherein the at least one biological parameter for the particular patient comprises normal tissue complication probability information.

5. The method of claim 1, wherein the at least one biological parameter for the particular patient comprises oxygen level information.

6. The method of claim 1, wherein the at least one biological parameter for the particular patient comprises linear energy transfer information.

7. The method of claim 1, wherein the at least one biological parameter for the particular patient comprises at least one of:
an identified tissue;
an identified organ;
a specified portion of an identified organ;
a temporal-based parameter;
a radiosensitivity of a given tissue/organ;
patient image information;
a tissue type;
a blood oxygen level;
a blood type;
a medication;
chemotherapy information;
prior surgery information;
immunotherapy information;
prior medical treatment information;
demographic information;
biological age information;
genetic marker information;
a time of day;
a tumor type;
pH (potential hydrogen) balance information;
temperature information;
blood pressure information;
blood panel information; and
immunity health information.

8. The method of claim 1, further comprising:
optimizing a FLASH radiation therapy treatment plan as a function, at least in part, of the determined biological equivalent dose for the particular patient to provide an optimized FLASH radiation therapy treatment plan.

9. The method of claim 8, further comprising:
administering radiation to the particular patient as a function of the optimized FLASH radiation therapy treatment plan.

10. The method of claim 8, further comprising:
quality evaluating the optimized FLASH radiation therapy treatment plan as a function, at least in part, of the determined biological equivalent dose for the particular patient.

11. The method of claim 1, further comprising:
generating a radiation treatment prescription as a function, at least in part, of the determined biological equivalent dose for the particular patient.

12. An apparatus comprising:
a memory having stored therein information representing a radiation dose deposition as a function of time for a particular patient and at least one biological parameter for the particular patient; and
a control circuit operably coupled to the memory and configured to:
access the information representing a radiation dose deposition as a function of time for a particular patient;
access the at least one biological parameter for the particular patient; and
determine a biological equivalent dose for the particular patient as a function of both the information representing a radiation dose deposition as a function of time for the particular patient and the at least one biological parameter for the particular patient to provide a determined biological equivalent dose for the particular patient.

13. The apparatus of claim 12, wherein the control circuit is configured to develop a biological equivalent dose for the particular patient by determining a plurality of biological equivalent doses for the particular patient as a function of both the information representing a radiation dose deposition as a function of time for the particular patient and the at least one biological parameter for the particular patient to thereby provide a plurality of determined biological equivalent doses for the particular patient.

14. The apparatus of claim 12, wherein the information representing a radiation dose deposition as a function of time for the particular patient comprises, at least in part, dose rate information.

15. The apparatus of claim 12, wherein the information representing a radiation dose deposition as a function of time for the particular patient comprises both dose information and dose rate information.

16. The apparatus of claim 12, wherein the at least one biological parameter for the particular patient comprises normal tissue complication probability information.

17. The apparatus of claim 12, wherein the at least one biological parameter for the particular patient comprises oxygen level information.

18. The apparatus of claim 12, wherein the at least one biological parameter for the particular patient comprises linear energy transfer information.

19. The apparatus of claim 12, wherein the at least one biological parameter for the particular patient comprises at least one of:
an identified tissue;
an identified organ;
a specified portion of an identified organ;
a temporal-based parameter;
a radiosensitivity of a given tissue/organ;

patient image information;
a tissue type;
a blood oxygen level;
a blood type;
a medication;
chemotherapy information;
prior surgery information;
immunotherapy information;
prior medical treatment information;
demographic information;
biological age information;
genetic marker information;
a time of day;
a tumor type;
pH (potential hydrogen) balance information;
temperature information;
blood pressure information;
blood panel information; and
immunity health information.

20. The apparatus of claim 12, wherein the control circuit is further configured to:
optimize a FLASH radiation therapy treatment plan as a function, at least in part, of the determined biological equivalent dose for the particular patient to provide an optimized FLASH radiation therapy treatment plan.

21. The apparatus of claim 20, wherein the control circuit is further configured to:
administer radiation to the particular patient as a function of the optimized FLASH radiation therapy treatment plan.

22. The apparatus of claim 20, wherein the control circuit is further configured to:
quality evaluate the optimized FLASH radiation therapy treatment plan as a function, at least in part, of the determined biological equivalent dose for the particular patient.

23. The apparatus of claim 12, wherein the control circuit is further configured to:
generate a radiation treatment prescription as a function, at least in part, of the determined biological equivalent dose for the particular patient.

* * * * *